United States Patent [19]

Smith et al.

[11] 4,120,898
[45] Oct. 17, 1978

[54] SULFUR CONTAINING VINYL AMIDE CROSS-LINKING AGENTS

[75] Inventors: Norman Alfred Smith, Hornchurch; Rainer Kitzing, Ingatestone, both of England

[73] Assignee: Ciba-Geigy AG, Basel, Switzerland

[21] Appl. No.: 760,291

[22] Filed: Jan. 18, 1977

[30] Foreign Application Priority Data

Feb. 4, 1976 [GB] United Kingdom ............... 4281/76

[51] Int. Cl.$^2$ ............... C07C 103/38; C07C 103/60; G03C 1/30
[52] U.S. Cl. ............... 260/561 S; 96/111; 260/112 R; 260/117; 260/553 R; 260/553 E; 260/561 K; 260/561 N; 427/145
[58] Field of Search ........... 260/553 R, 553 E, 561 K, 260/561 S, 117

[56] References Cited

U.S. PATENT DOCUMENTS

| | | | |
|---|---|---|---|
| 3,455,892 | 7/1969 | Froehlich | 260/553 R X |
| 3,455,893 | 7/1969 | Froehlich | 260/117 |
| 3,490,911 | 1/1970 | Burness et al. | 260/117 X |
| 3,547,899 | 12/1970 | Arlt et al. | 260/561 S X |
| 3,551,159 | 12/1970 | Froehlich | 260/553 E X |
| 3,574,709 | 4/1971 | Froehlich | 260/553 E X |
| 3,641,116 | 2/1972 | Froehlich | 260/553 E X |
| 3,687,698 | 8/1972 | Cohen | 260/117 X |
| 3,841,872 | 10/1974 | Burness et al. | 260/117 X |
| 3,868,257 | 2/1975 | Horii et al. | 260/117 X |
| 3,977,881 | 8/1976 | Kyburz et al. | 260/553 E X |
| 3,978,122 | 8/1976 | Stauner et al. | 260/553 E |
| 3,989,842 | 11/1976 | Wellings et al. | 260/553 E X |
| 4,001,201 | 1/1977 | Kyburz | 260/117 |
| 4,002,710 | 1/1977 | Hammer et al. | 260/117 X |
| 4,011,201 | 3/1977 | Ponticello | 260/561 K X |
| 4,028,320 | 6/1977 | Sera et al. | 60/117 |
| 4,039,520 | 8/1977 | Habu et al. | 260/533 C X |

Primary Examiner—Winston A. Douglas
Assistant Examiner—Thomas A. Waltz
Attorney, Agent, or Firm—Burgess, Dinklage & Sprung

[57] ABSTRACT

New vinyl compounds of the general formula

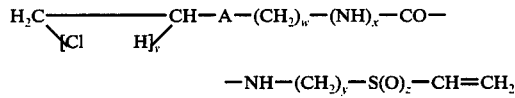

$$-NH-(CH_2)_y-S(O)_z-CH=CH_2$$

are provided, wherein A is —CO— or —SO$_2$—, $v$ is 0 or 1, $w$ is 0 or an integer of 1 to 6, $x$ is 0 or 1, $y$ is 2 to 6 and $z$ is 1 or 2, at least one of $w$ and $x$ x being a positive integer. The vinyl compounds are useful as cross-linking agents for hydrophylic colloids, especially for gelatine in gelatino silver halide emulsion layers and other layers in photographic material.

3 Claims, No Drawings

SULFUR CONTAINING VINYL AMIDE CROSS-LINKING AGENTS

This invention relates to novel vinyl compounds, their production and to their use as cross-linking agents for hydrophilic colloids.

According to the present invention there are provided vinyl compounds of the general formula

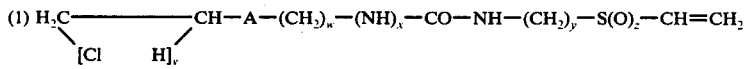

wherein A is —CO— or —SO$_2$—, $v$ is 0 or 1, $w$ is 0 or an integer of 1 to 6, $x$ is 0 or 1, $y$ is 2 to 6 and $z$ is 1 or 2, at least one of $w$ and $x$ being a positive integer.

Particularly useful compounds of formula (1) are those wherein A is —CO—, $w$ is 0 and $x$ is 1. Other compounds of particular interest are those wherein A is —SO$_2$—, $w$ is 2 or 3 and $x$ is 0.

Compounds of formula (1) wherein $v$ is 1, A is —CO—, $w$ is 0, $x$ is 1, $y$ is 2 or 3 and $z$ is 1 or 2 may be prepared by reacting an amine of the general formula $$NH_2-(CH_2)_y-S-CH=CH_2 \qquad (2)$$

where $y$ has the meaning assigned to it above with β-chloropropionyl-isocyanate to yield a compound of the formula $$ClCH_2-CH_2-CO-NH-CO-NH-(CH_2)_y-S-CH=CH_2 \qquad (3)$$

and then oxidising the sulphur atom to yield either the sulphoxide or the sulphone compound.

Compounds of formula (3) may be oxidised with a hydrogen peroxide/acetic acid mixture to yield the sulphoxide and with peracetic acid to yield the sulphone.

The compounds formed by this reaction may be converted to the corresponding bis-vinyl compounds by dehydrochlorination. There are a number of well known dehydrochlorination methods for example the method using triethylamine which is described in U.S. Pat. No. 3,868,257.

The compounds of the general formula (1) wherein $v$ is 1, A is —SO$_2$—, $w$ is 2 to 6, $x$ is 0, $y$ is 2 to 6, and $z$ is 1 or 2 may be prepared by reacting the amine of formula (2) with an acyl chloride of formula $$CL-CH_2-CH_2-SO_2-(CH_2)_w-CO-Cl \qquad (4)$$

to yield a compound of the formula $$Cl-CH_2-CH_2-SO_2-(CH_2)_w-CO-NH-(CH_2)_y-S-CH=CH_2 \qquad (5)$$

and then oxidising the sulphur atom to yield either the sulphoxide or the sulphone compound.

The compounds formed by this reaction may be converted to the corresponding bis-vinyl compounds by dehydrochlorination.

The symmetrical compounds of formula (1) which have the formula $$CH_2=CH-SO_2-(CH_2)_w-NH-CO-NH-(CH_2)_y-SO_2-CH=CH_2 \qquad (6)$$

wherein $w$ and $y$ are the same integers, each of which being 1 to 6, may be prepared by reacting two parts of the amine of formula (2) with one part of phosgene to yield a compound of the general formula $$CH_2=CH-S-(CH_2)_w-NH-CO-NH-(CH_2)_y-S-CH=CH_2 \qquad (7)$$

and then oxidising the sulphur atoms to yield the bis-vinyl sulphone compound.

Similar compounds to those of formula (6) but wherein $w$ need not be the same as $y$ may be prepared by reacting an amine of formula (2) with phosgene under controlled conditions to form an isocyanate of the formula $$CH_2=CH-S-(CH_2)_w-N=C=O \qquad (8)$$

and then reacting the isocyanate with an amine of formula (2) to produce a compound of the general formula $$CH_2=CH-S-(CH_2)_w-NH-CO-NH-(CH_2)_y-S-CH=CH_2 \qquad (9)$$

and then oxidising to yield the bis-vinyl sulphone compound.

The compounds of formula (1) are of particular use in cross-linking hydrophilic colloids.

Therefore according to another aspect of the present invention there is provided a process for cross-linking hydrophilic colloids which contain amino, imino and-/or hydroxyl groups characterised in that at least one compound of the above formula (1) is incorporated into the colloid to effect cross-linking thereof.

The cross-linking process of the present invention can be used in the textile and leather industry, the manufacture of paper and the plastics, glue and gelatine industry. Above all, it can be used as a process for hardening water-soluble colloids for example polyvinyl alcohol, gelatine or gelatin derivatives, especially when these colloids are in the form of layers of photographic materials. The reaction of these colloids with the vinyl compounds of the present invention takes place easily, and in the usual manner. The vinyl compounds are water-soluble and thus can be used as aqueous solutions.

However the vinyl compounds of formula (1) vary greatly in their rate of hardening hydrophilic colloids. The compounds containing a terminal chloro-ethyl group Cl—CH$_2$—CH$_2$— are less reactive than similar compounds having two terminal vinyl groups.

The vinyl sulphone compounds are more reactive than the corresponding vinyl sulphoxide compounds, for example the compounds of formula (1) wherein $z$ is 2 are more reactive than those wherein $z$ is 1. The compounds of formula (1) wherein A is —SO$_2$— are more reactive than the compounds of formula (1) wherein A is —CO—.

Thus the most reactive compounds of formula (1) are the compounds of formula $$CH=CH-SO_2-(CH_2)_w-CO-NH-(CH_2)_x-SO_2-CH=CH_2 \qquad (10)$$

wherein $w$ and $y$ are 2 or 3 and the least reactive compounds of formula (1) are the compounds of formula $$Cl-CH_2-CH_2-CO-NH-CO-NH-(CH_2)_y-SO-CH=CH_2 \qquad (11)$$

wherein $y$ is 2 to 6, preferably 2 or 3.

Other compounds of formula (1) have reactivities between those of the compounds of formulae (10) and (11).

In practice the most useful compounds of formula (1) are those having one active terminal group ($-CH=CH_2$) and one not very active terminal group ($Cl-CH_2-CH_2-$), for example the compound of formula $$Cl-CH_2-CH_2-CO-NH-CO-NH-(CH_2)_3-SO_2-CH=CH_2 \qquad (12).$$

When compounds of this type are incorporated into hydrophilic colloids the vinyl sulphone end group links with the colloid very rapidly but the chloro-ethyl end group acts very slowly and thus cross-linking with the colloid only takes place slowly.

However, it is possible to accelerate the activity of the not very active end group in a number of ways for example by the application of heat, moisture or raising the pH. Compounds of this type are of use for example when the colloid to be cross-linked is present as a layer in coated layer material and it is desired that not all the layers should be hardened or cross-linked to the same extent. For example if the colloid to be cross-linked is gelatin the compound of formula 12 is added to an aqueous gelatine solution. This compound attaches itself to the gelatine by reaction of the vinyl sulphone end group with amino groups present in the gelatine. However the gelatine is not cross-linked and thus its viscosity does not increase substantially and the gelatine solution can be coated as a layer on a base. Other hydrophilic colloid layers may also be present on the base either above or below the layer containing the vinyl sulphone compound. Thus the compound will not migrate substantially from the gelatine of a layer in which it was incorporated because it is attached to the gelatin. Subsequently it is possible to harden this gelatine layer by the application of heat to the coated layer. This heat will activate the non-active chloro-ethyl group and a cross-linking of the gelatine will take place. The gelatin layer only will be cross-linked or hardened. Thus the compounds of formula (1) which have an active terminal group and an inactive terminal group can be used as so-called layer specific hardeners for hydrophilic colloid layers.

Usually in order to carry out the cross-linking process of the present invention if suffices to add the vinyl compounds of the present invention as an aqueous solution or in solid form which is a finely divided as possible, to an aqueous solution of the hydrophilic colloid, with good stirring.

Thus, a solution of the vinyl cross-linking agent in water, or mixed with, for example, ethanol, methanol or acetone, can be brought together with the colloids at normal or slightly raised temperature. Gelatine, which optionally may contain silver halide and/or other components required to produce photographic images, has proved particularly suitable for cross-linking by the process of the present invention.

The coating solution which is an aqueous solution containing both gelatine and the vinyl cross-linking agent can, in the usual way, be coated on a substrate to form a layer, and be dried. The layer can then be left at elevated temperature or at room temperature for a certain time, for example up to 24 hours. Thereupon cross-linking, which is evidenced by hardening of the layer, takes place and this is shown by the melting point of the gelatin being raised substantially, for example from 25° to 60° C., and by the reciprocal swelling factor increasing.

The amount of the vinyl cross-linking agent used depends on the desired degree of hardening of the gelatine layer required but is suitably from 0.1 to 10 percent by weight based on the weight of the dry gelatin.

A particular advantage of the process of the present invention is that when the vinyl cross-linking agents are used at low concentration they impart a sufficient degree of hardness to the gelatin layers in 18 to 24 hours, so that the coated material can be tested by processing a sample immediately following its manufacture, even if the test be carried out at a raised temperature or in strong processing baths.

It is a further advantage that during the process of the present invention, no significant change in pH of the gelatine layer occurs.

The cross-linking or hardening effect itself is very stable; even after prolonged storage at temperatures around 40° C. and at a relative atmoshperic humidity of about 70% (Compare Table)

Further the degree of hardening is also not changed significantly by acids or bases even on prolonged action, which indicates that the hardener-gelatine bond created has great resistance to hydrolysis.

The vinyl compounds of the present invention are furthermore generally sufficiently soluble in water and sufficiently stable in aqueous solutions to enable the process of the present invention to be used in the preparation of photographic material. Thus, for example, it is desirable — particularly for the continuous manufacture of photographic materials — that batches of solutions of cross-linking agents should remain stable at room temperature for several hours or days and that its concentration should not decrease or should only do so insignificantly. Also it is important that in the coating solution, at about 40° C., the hardener should undergo very little or no decomposition and very little or no reaction with water during the requisite standing time and dwell time, so as to maintain its full cross-linking action over the course of several hours, during coating, drying and storage of the photographic material.

Furthermore, the viscosity of the coating solution should not significantly increase during the standing time as a result of the addition of the hardener.

The compounds of formula (1) having one active end group and one not very active end group cause hardly any change in viscosity as just explained but the compounds of formula (1) having two active end groups raise the viscosity of coating solution very rapidly. It is also particularly important that even on prolonged treatment of the coated layer at raised temperature and atmospheric humidity conditions the hardener should not cause any yellowing, fogging of photographic material or effect on the graduation of the material on development.

The vinyl compounds of the present invention fulfil the above desiderata very well. In particular they hydrolyse very little when present in an aqueous solution. They do not discolour gelatin. Further when certain of these compounds are added to a gelatine solution they cause only a small increase in the viscosity of the solution and thus such solutions can be coated without difficulty. The compounds have a good hardening effect over a wide pH range and thus can be used in the preparation of a wide range of photographic materials.

Thus the process of the present invention is suitable for hardening (cross-linking) all the layers in photographic material containing gelatin for example, intermediate layers, emulsion layers, base layers, top layers, backing layers and anti-halation layers. The layers can contain not only the cross-linking agents but also the additives of the most diverse kind for example, silver halide, pigments, such as barium sulphate, titanium dioxide or silicon dioxide or those of organic nature, such as coloured pigments, and also image dyestuffs, colour coupling agents, latices, mordants sensitisers, filter dyestuffs, anti-halation dyestuffs and light screening dyestuffs, emulsion stabilisers, UV absorbers, optical brighteners and even other cross-linking agents.

The present invention not only includes the novel vinyl compounds of formula (1), the process for preparing these compounds, the process for cross-linking hydrophilic colloids using the vinyl compounds of formula (1) but also includes hydrophilic colloids cross-linked by the above cross-linking process and in particular includes layers containing gelatin so cross-linked especially gelatino silver halide emulsion layers and other layers in photographic material as well as the photographic material containing such layers.

EXAMPLE 1

1,3-Bis-[3-vinyl-thio-propyl]-urea (Intermediate 1)

A mixture of 2.5 g 3 vinyl-thio-propylamine, 1.5 g sodium carbonate and 15 ml water was stirred at room temperature while 1.0 g of phosgene was passed in. The white precipitate was filtered off, washed with water and dries. Yield 2.1 g; Mp. 60° to 63° C.

1,3 Bis-[3-vinyl-sulphonyl-propyl]-urea (Hardener 1)

2.0 g Intermediate 1 to 10 ml glacial acid was treated with 6 ml of 40 % peracetic acid and 10 ml water at 5° to 10° C. After stirring 4 hours and leaving 15 hours at room temperature the solution was evaporated under reduced pressure and the residue stirred with 20 ml acetone then filtered. The filtrate was evaporated and the viscous product stirred with 50 ml dry ether. The solid was filtered off and recrystallised from ethyl acetate. Yield 1.1 g; Mp. 95° to 96° C.

EXAMPLE 2

3-(2-Chlorethylsulphonyl)-N-(2-vinylthioethyl)-propionamide (Intermediate 2)

A solution of 5.92 g 3-(2-chloroethylsulphonyl)-propionyl chloride in 75 ml dichloromethane was treated dropwise with a solution of 2.65 g 2-vinylthioethylamine and 2.6 g triethylamine in dichlormethane. After 2 hours, the solution was evaporated and the residue recrystallised from aqueous ethanol. Yield 6.1 g; Mp. 102° to 103° C.

3-(2-Chloroethylsulphonyl)-N-(2-vinylsulphinylethyl)-propionamide (Hardener 2)

A suspension of 6 g Intermediate 2 in 25 ml acetic acid was treated at 20° C. with 2.5 ml of 30 % hydrogen peroxide and 3 ml acetic acid. After 2 hours the solution was evaporated and the residue stirred with ether. The solid was filtered, dried and recrystallised from ethanol-petrolether. Yield 4.85 g; Mp. 108° to 109° C.

EXAMPLE 3

3-(Vinylsulphonyl)-N-(2-vinylsulphinyl-ethyl)-propionamide. (Hardener 3)

0.8 g Triethylamine was added to a solution of 2.0 g Intermediate 2 in 10 ml dimethylformamide. After stirring 1 hour the mixture was filtered and the filtrate evaporated. The residue was recrystallised form ethyl acetate and then from dichloromethanepetrolether. Yield 1.1 g; Mp. 93° C.

EXAMPLE 4

3-(2-Chloroethylsulphonyl)-N-(2-vinylsulphonylethyl)-propionamide (Hardener 4)

A solution of 2.0 g Hardener 2 in 6 ml acetic acid was oxidised with 1.3 ml of 40 % peracetic acid. After 15 hours at room temperature, 10 ml water was added to the solution, the solid filtered off and dried. Recrystallisation from ethanol gave 1.45 g product. Mp. 113° C. to 114° C.

3-(2-Chloroethylsulphonyl)-N-(3-vinylsulphonyl-propyl)-propionamide (Hardener 10) was prepared similarly except that in the preparation of the intermediate vinylthiopropyiamine was used instead of vinylthioethylamine.

EXAMPLE 5

3-(Vinylsulphonyl)-N-(vinylsulphonylethyl)-propionamide (Hardener 5)

1.0 g Hardener 4 in 4 ml dimethyl formamide was treated with 0.4 g triethylamine. The mixture was stirred for 1 hour then filtered. The filtrate was evaporated and the residue dissolved in 10 ml ice-cold ethyl acetate. The mixture was filtered and the filtrate evaporated to give 0.85 g of a non-crystallisable oil.

EXAMPLE 6

1-(3-Chlorpropionyl)-3(2-vinylthioethyl)-urea (Intermediate 6)

4.0 g redistilled 3-chloropropionyl isocyanate in 30 ml toluene at 0° to 5° C. was treated dropwise with 3.1 g 2 vinylthioethylamine in toluene. After 30 minutes the mixture was filtered and the solid recrystallised from methanol. Yield 3.7 g; Mp 100° to 101° C.

1-(3-chloropropionyl)-3-(2-vinylsulphinylethyl)-urea (Hardener 6)

4.05 g Intermediate 6 in 20 ml acetic acid was oxidised with 30 % hydrogen peroxide in the usual way. After 2 hours, the solution was evaporated and the residue stirred with ether. The solidified product was filtered off and recrystallised from ethanolpetrolether. Yield 3.1 g; Mp. 113° to 135° C.

EXAMPLE 7

1-Acryloyl-3-(2-vinylsulphinylethyl)-urea. (Hardener 7)

1.0 g Hardener 6 in dimethylformamide was treated in the usual way with 0.5 g triethylamine. Recrystallisation from ethyl acetate-petrolether then from dichloroethane-petrolether yielded 0.4 g product. Mp. 109° to 110° C.

EXAMPLE 8

1-(3-chloropropionyl)-3-(2-vinylsulphonylethyl)-urea (Hardener 8)

1.72 g Hardener 6 in acetic acid was oxidised with peracetic acid in the usual way. Evaporation of the reaction mixture left a viscous residue which solidified on stirring with 10 ml water. The product was filtered off, dried and recrystallised from ethyl acetate-petrolether. Yield 1.27 g; Mp. 122° to 124° C.

1-(3-chloropropionyl)-3-(2-vinylsulphonylpropyl)-urea (Hardener 11) was prepared in a similar manner except that vinylthiopropylamine was used in the preparation of the intermediate in the place of vinylthioethylamine.

1-acryloyl-3-(2-vinylsulphonylpropyl)-urea (Hardener 12) was prepared from the above compound by treatment with triethylamine in dimethyl formamide.

EXAMPLE 9

1-Acryloyl-3-(vinylsulphonylethyl)-urea (Hardener 9)

1.0 g Hardener 8 in dimethyl formamide was treated as before with 0.45 g triethylamine. Recrystallisation from ethyl acetate and then from 1,2 dichloroethane. Yield 0.4 g product; Mp. 177° to 179° C.

EXAMPLE 10

In the Example which follows, the reciprocal swelling factor is used as a measure of the hardening. The samples were prepared as follows: 6 ml of a 6 % strength gelatine solution, 1 ml of a 1 % strength dyestuff solution of the formula

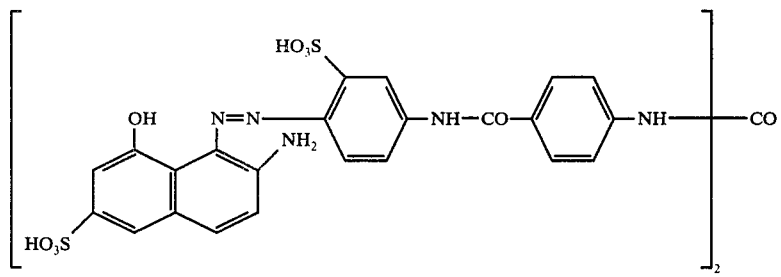

1 ml of a $25.10^{-3}$ molar solution of hardener 1 and 5 ml of deionise water are mixed and the pH adjusted to 6.5. The solution is coated on a 13 × 18 cm triacetate film. After solidification at 10° C., the layer is dried over the course of 2 hours at approx. 20° C. (The dyestuff merely serves to make the samples more readily visible during the swelling measurements.) Some samples of the coated film were stored under room conditions. (NK, approx. 20° C., 50 % relative atmospheric humidity) and other samples were incubated (CL, 43° C., 69 % relative atmospheric humidity). Similar solutions of hardeners 2 to 12 were also prepared and tested.

To determine the reciprocal swelling factor, a thin section of approx. 20μ is prepared from each of the samples and measured under a microscope. The thickness of the dry gelatin layer is then determined, deionised water is then added and after 4 minutes the thickness of the swollen gelatin layer is measured. The reciprocal swelling factor 1/SF corresponds to the following ratio:

$$\frac{1}{SF} = \frac{\text{Thickness of the dry layer.}}{\text{Thickness of the swollen layer.}}$$

Table.

| Hardener | Storage | 1/SF 2 Days | 7 Days | 14 Days | 28 Days |
|---|---|---|---|---|---|
| 1 | NK | 0.11 | 0.20 | 0.25 | 0.29 |
|   | CL | 0.37 | 0.38 | 0.38 | 0.46 |
| 2 | NK | 0.07 | 0.05 | 0.11 | 0.10 |
|   | CL | 0.12 | 0.12 | 0.22 | 0.23 |
| 3 | NK | 0.07 | 0.08 | 0.09 | 0.10 |
|   | CL | 0.16 | 0.15 | 0.20 | 0.27 |
| 4 | NK | 0.17 | 0.25 | 0.27 | 0.33 |
|   | CL | 0.40 | 0.40 | 0.41 | 0.44 |
| 5 | NK | 0.21 | 0.24 | 0.28 | 0.32 |
|   | CL | 0.29 | 0.36 | 0.37 | 0.34 |
| 10 | NK | 0.16 | 0.18 | 0.21 | 0.23 |
|   | CL | 0.24 | 0.25 | 0.26 | 0.28 |
| 6 | NK | — | 0.05 | 0.06 | 0.08 |
|   | CL | — | 0.14 | 0.19 | 0.26 |
| 7 | NK | — | 0.06 | 0.05 | 0.08 |
|   | CL | — | 0.17 | 0.19 | 0.26 |
| 8 | NK | 0.10 | 0.20 | 0.20 | 0.28 |
|   | CL | 0.36 | 0.42 | 0.35 | 0.41 |
| 9 | NK | 0.17 | 0.26 | 0.25 | 0.31 |
|   | CL | 0.36 | 0.40 | 0.40 | 0.45 |
| 11 | NK | 0.06 | 0.14 | 0.20 | 0.30 |
|   | CL | 0.33 | 0.36 | 0.38 | 0.39 |
| 12 | NK | 0.16 | 0.25 | 0.27 | 0.30 |
|   | CL | 0.38 | 0.37 | 0.39 | 0.40 |

We claim:
1. A vinyl compound of the general formula

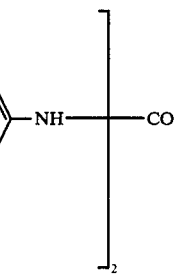
$$-NH-(CH_2)_y-S(O)_z-CH=CH_2$$

wherein $v$ is 0 or 1, $w$ is 2 or 3 $y$ is 2 to 6 and $z$ is 1 or 2.

2. A vinyl compound according to claim 1 wherein $v$ is 0 and $w$ is 2 or 3.

3. A vinyl compound according to claim 1 of the general formula $$CH_2=CH-SO_2-(CH_2)_w-CO-NH-(CH_2)_y-SO_2-CH=CH_2$$

wherein $w$ and $y$ are 2 or 3.

* * * * *